(12) United States Patent
Comber et al.

(10) Patent No.: US 9,492,234 B2
(45) Date of Patent: Nov. 15, 2016

(54) MOTIVE DEVICE FOR USE IN MAGNETICALLY-SENSITIVE ENVIRONMENTS

(71) Applicants: David B. Comber, Nashville, TN (US); Eric J. Barth, Nashville, TN (US)

(72) Inventors: David B. Comber, Nashville, TN (US); Eric J. Barth, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 785 days.

(21) Appl. No.: 13/679,512

(22) Filed: Nov. 16, 2012

(65) Prior Publication Data
US 2013/0123802 A1    May 16, 2013

Related U.S. Application Data

(60) Provisional application No. 61/560,496, filed on Nov. 16, 2011.

(51) Int. Cl.
*A61B 19/00* (2006.01)
*A61B 17/00* (2006.01)

(52) U.S. Cl.
CPC ........... *A61B 19/2203* (2013.01); *A61B 34/30* (2016.02); *A61B 2017/00292* (2013.01); *A61B 2017/00318* (2013.01); *A61B 2017/00544* (2013.01); *A61B 2034/301* (2016.02); *A61B 2034/303* (2016.02); *A61B 2090/3954* (2016.02)

(58) Field of Classification Search
CPC ................ A61B 2017/00292; A61B 19/2203; A61B 2019/2211; A61B 2019/2219; A61B 34/30; A61B 2017/00318
See application file for complete search history.

(56) References Cited

U.S. PATENT DOCUMENTS

| 4,723,545 A | * | 2/1988 | Nixon | A61B 17/320016 600/568 |
| 2003/0195436 A1 | * | 10/2003 | Van Bladel | A61B 10/0266 600/584 |
| 2003/0199787 A1 | * | 10/2003 | Schwindt | A61M 1/0058 600/568 |
| 2006/0184063 A1 | * | 8/2006 | Miller | A61B 10/0266 600/568 |
| 2007/0060879 A1 | * | 3/2007 | Weitzner | A61B 17/12045 604/95.04 |
| 2007/0167736 A1 | * | 7/2007 | Dietz | A61B 10/0275 600/411 |

FOREIGN PATENT DOCUMENTS

| WO | 2009094670 | 7/2009 |
| WO | 2011063511 | 6/2011 |

* cited by examiner

*Primary Examiner* — Corrine McDermott
*Assistant Examiner* — Sarah Simpson
(74) *Attorney, Agent, or Firm* — Tarolli, Sundheim, Covell & Tummino LLP

(57) ABSTRACT

A motive device for use in magnetically sensitive environments includes a front supporting plate, a rear supporting plate, and at least one guiding rail extending longitudinally between the front and rear supporting plates and supported thereby. At least one module is supported by the guiding rail, is located longitudinally between the front and rear supporting plates, and is configured to provide at least one of translational and rotational motions to a moved structure extending from the at least one module longitudinally toward and beyond the front supporting plate. The translational motion is guided by motion of the module between the front and rear supporting plates longitudinally along the at least one guiding rail. The module provides the at least one of translational and rotational motions to the moved structure entirely pneumatically. The structures comprising the motive device are all made entirely from non-ferromagnetic materials.

11 Claims, 12 Drawing Sheets

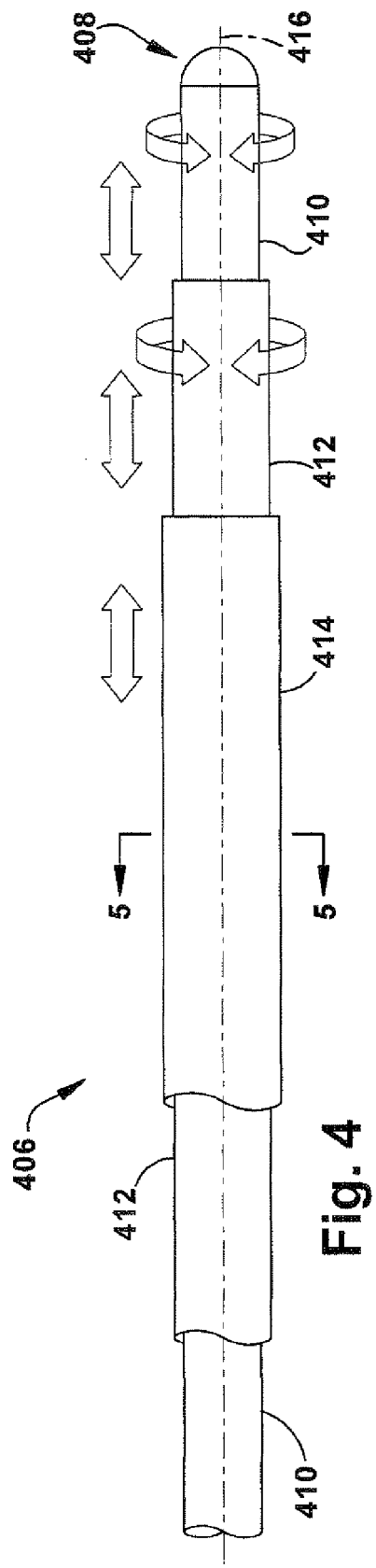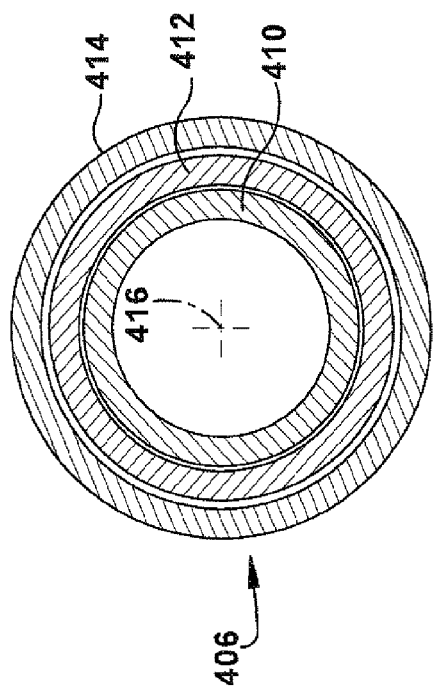
Fig. 4
Fig. 5

MOTIVE DEVICE FOR USE IN MAGNETICALLY-SENSITIVE ENVIRONMENTS

RELATED APPLICATION

This application claims priority from U.S. Provisional Application No. 61/560,496, filed 16 Nov. 2011, the subject matter of which is incorporated herein by reference in its entirety.

TECHNICAL FIELD

The present invention relates to an apparatus and method for use of a motive device for use in magnetically-sensitive environments and, more particularly, to a robotic device configured for use in or near a magnetic resonance imaging device.

BACKGROUND OF THE INVENTION

Magnetic resonance imaging, nuclear magnetic resonance imaging, or magnetic resonance tomography are medical imaging techniques used in radiology to visualize detailed internal structures—the term "MRI" will be used herein to reference all of these and related technologies. MRI makes use of the property of nuclear magnetic resonance to image nuclei of atoms inside the body.

An MRI machine uses a powerful magnetic field to align the magnetization of some atoms in the body, and radio frequency fields to systematically alter the alignment of this magnetization. This causes the nuclei to produce a rotating magnetic field detectable by the scanner, and this information is recorded to construct an image of the scanned area of the body. Strong magnetic field gradients cause nuclei at different locations to rotate at different speeds. 3-D spatial information can be obtained by providing gradients in each direction.

MRI provides good contrast between the different soft tissues of the body, which makes it especially useful in imaging the brain, muscles, the heart, and cancers compared with other medical imaging techniques such as computed tomography (CT) or X-rays. Unlike CT scans or traditional X-rays, MRI uses no ionizing radiation. The very high strength of the magnetic field however, can cause "missile-effect" accidents, where ferromagnetic objects are attracted to the center of the magnet, and there have been incidences of injury and death due to the strong magnetic fields generated by the MRI device. To reduce the risks of projectile accidents, ferromagnetic objects and devices are typically prohibited in proximity to the MRI machine and patients undergoing MRI examinations are required to remove all ferrometallic and ferromagnetic objects from their vicinity and apparel. Ferromagnetic detection devices are used by some sites in an attempt to avoid the introduction of ferromagnetic objects into the vicinity of the MRI machine, as well.

Moreover, in addition to possibly adverse physical movement of ferromagnetic objects located in proximity to the MRI machine, such objects may also provide image artifacts and/or geometric distortions which can cause difficult-to-read or even misleading MRI test results. During imaging it is also possible for metallic objects inside the MRI machine to heat up due to eddy currents, and this concern for patient safety also constrains material selection for MRI-guided devices. Due to the desire of the user to have highly accurate and precise MRI images, such unwanted side effects of ferromagnetic, ferrometallic, and/or metallic presence may prevent certain procedures from being guided by MRI. Additionally or alternatively, MRI images obtained in the presence of ferromagnetic objects may be unsuitable and need to be repeated later (if possible), which can cause unwanted expense and/or delay in treatment of a patient.

Thermal ablation is an interventional technique that helps to enable percutaneous treatment of many cancers and other disorders throughout the human body. Acoustic ablation can help steer thermal energy electronically and is known to be MRI-compatible. Therefore, acoustic ablation may be amenable to real-time thermal dose monitoring via MRI-assisted thermometry.

In the neurological field, active cannulae are sometimes used for percutaneous interventions, such as for acoustic and other thermal ablations, biopsies, deep brain stimulation, electrode placement, or for any other desired reason(s). An example of an active cannula is given in U.S. Patent Application Publication No. 2009/0171271, published Jul. 2, 2009 by Robert James Webster et al. This and other active cannulae include a plurality of concentric or nested tubes which may each have preformed curvatures and/or predefined flexibilities. The translation and/or angular orientation (rotation) of each tube may be controlled individually such that the tubes can telescope and twist to move the tip of the cannula into a desired orientation along a desired path. The tip of the cannula may contain, carry, orient, or otherwise provide positional assistance to an "end effector", which is a tool such as a biopsy gun, ablator, electrode, electrode positioner, camera, fiber-optic lens, or any other suitable tool which may be used to perform some task at, and/or have some effect upon, an area of the patient tissue to which the active cannula carries this "end effector", preferably in a precise and accurate manner for most use environments of the present invention.

It may be desirable for an active cannula to be precisely steered, moved, and controlled in certain use environments, particularly in neurosurgical interventions, such as, for example, in the application of ablative energy. The desired precise motion of the active cannula may be facilitated robotically in surgical environments, as robots can be controlled to sub-millimetric precision. MRI imaging and guidance would be helpful in observing and directing the movement of the active cannula, but the robots currently available for cannula guidance are lacking in MRI-compatibility. Currently available robots actuated by piezoelectric motors cannot truly operate in real time in an MRI environment because the high voltage power supply to the motors cannot be energized while the MRI machine is imaging due to potential distortion effects. Furthermore, MRI-compatible robots employing piezoelectric or hydraulic actuation are not easily integrated into existing hospital facilities due to the unfamiliarity of maintenance and operating personnel with these power sources. In addition, hydraulically-actuated MRI-compatible robots require a steady supply of hydraulic fluid, which both is not generally available in a hospital environment (thus, must be separately stocked and managed) and also can cause a mess, slipping hazard, or even contamination of a patient's body if it leaks out of the robot system within the hospital environment.

SUMMARY OF THE INVENTION

In an embodiment of the present invention, a motive device for use in magnetically sensitive environments is described. The motive device comprises a front supporting plate, a rear supporting plate, and at least one guiding rail extending longitudinally between the front and rear supporting plates and supported thereby. At least one module is supported by the guiding rail, is located longitudinally between the front and rear supporting plates, and is configured to provide at least one of translational and rotational motions to a moved structure extending from the at least one module longitudinally toward and beyond the front supporting plate. The translational motion is guided by motion of the module between the front and rear supporting plates longitudinally along the at least one guiding rail. The module provides the at least one of translational and rotational motions to the moved structure entirely pneumatically. The structures comprising the motive device are all made entirely from non-ferromagnetic materials.

In an embodiment of the present invention, a method of operating an active cannula is provided. The active cannula comprises innermost, middle, and outermost concentrically nested tubes collectively defining a longitudinal tube axis. A motive device comprising a front supporting plate, a rear supporting plate, and at least one guiding rail extending longitudinally between the front and rear supporting plates and supported thereby is provided. First, second, and third modules are supported by the guiding rail and are located in longitudinal series between the front and rear supporting plates. The structures comprising the motive device are all made entirely from non-ferromagnetic materials. The innermost tube is operatively coupled to the first module. The middle tube is operatively coupled to the second module. The outermost tube is operatively coupled to the third module. At least one of translational and rotational motions is provided, entirely pneumatically using the first, second, and third modules, to a respective innermost, middle, and outermost tube extending from the respective module longitudinally toward and beyond the front supporting plate. Translational motion of at least one of the innermost, middle, and outermost tubes is guided along the at least one guiding rail through motion of at least one respective first, second, and third module.

BRIEF DESCRIPTION OF THE DRAWINGS

For a better understanding of the invention, reference may be made to the accompanying drawings, in which:

FIG. 4 is a schematic side view of an example moved structure for use with the embodiment of FIG. 1;

FIG. 5 is a cross-sectional view taken along line 5-5 of FIG. 4;

DESCRIPTION OF EMBODIMENTS

Figure 1:
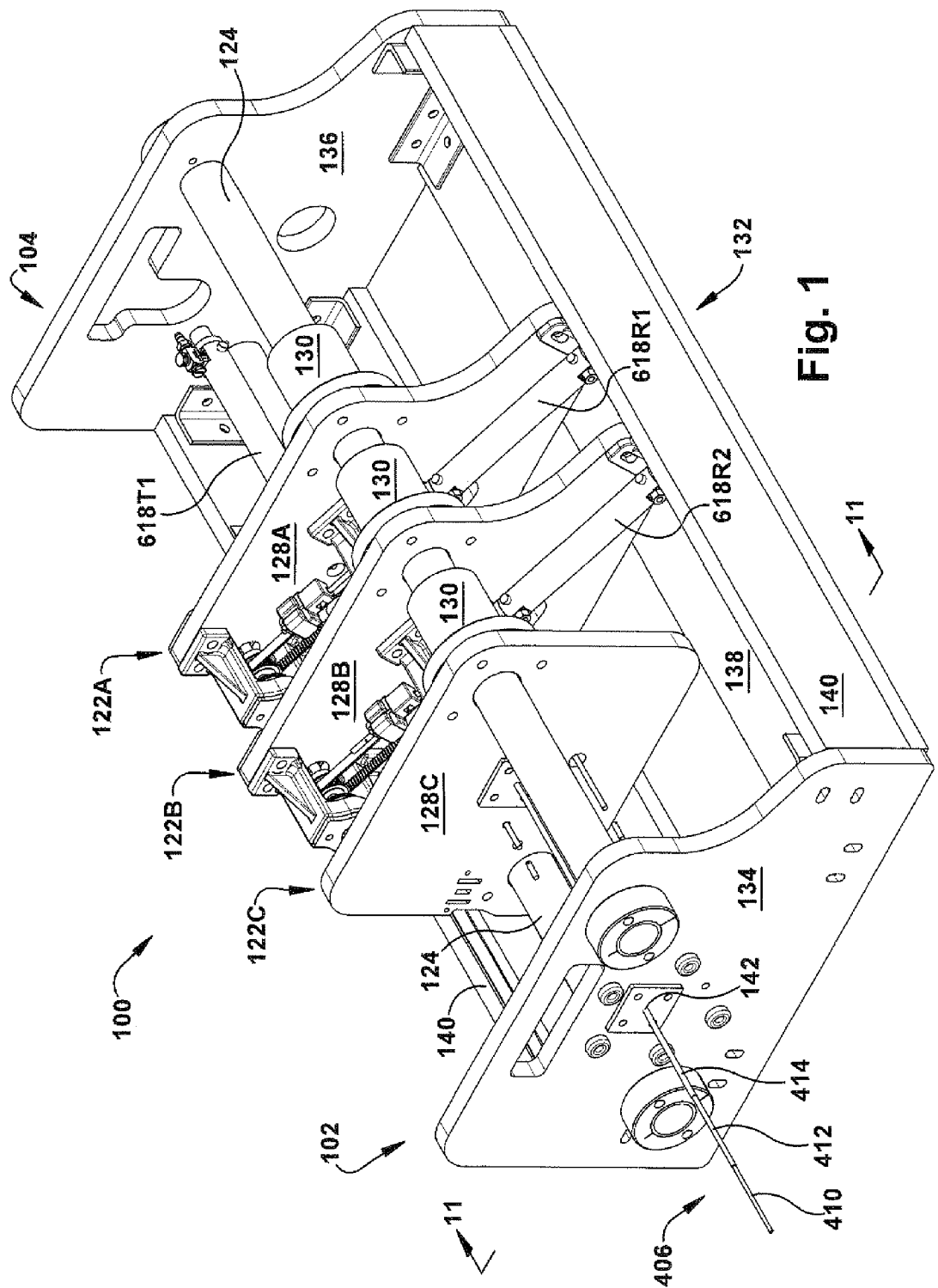
FIG. 1 is a perspective top view of an embodiment of the present invention.
Figure 2:
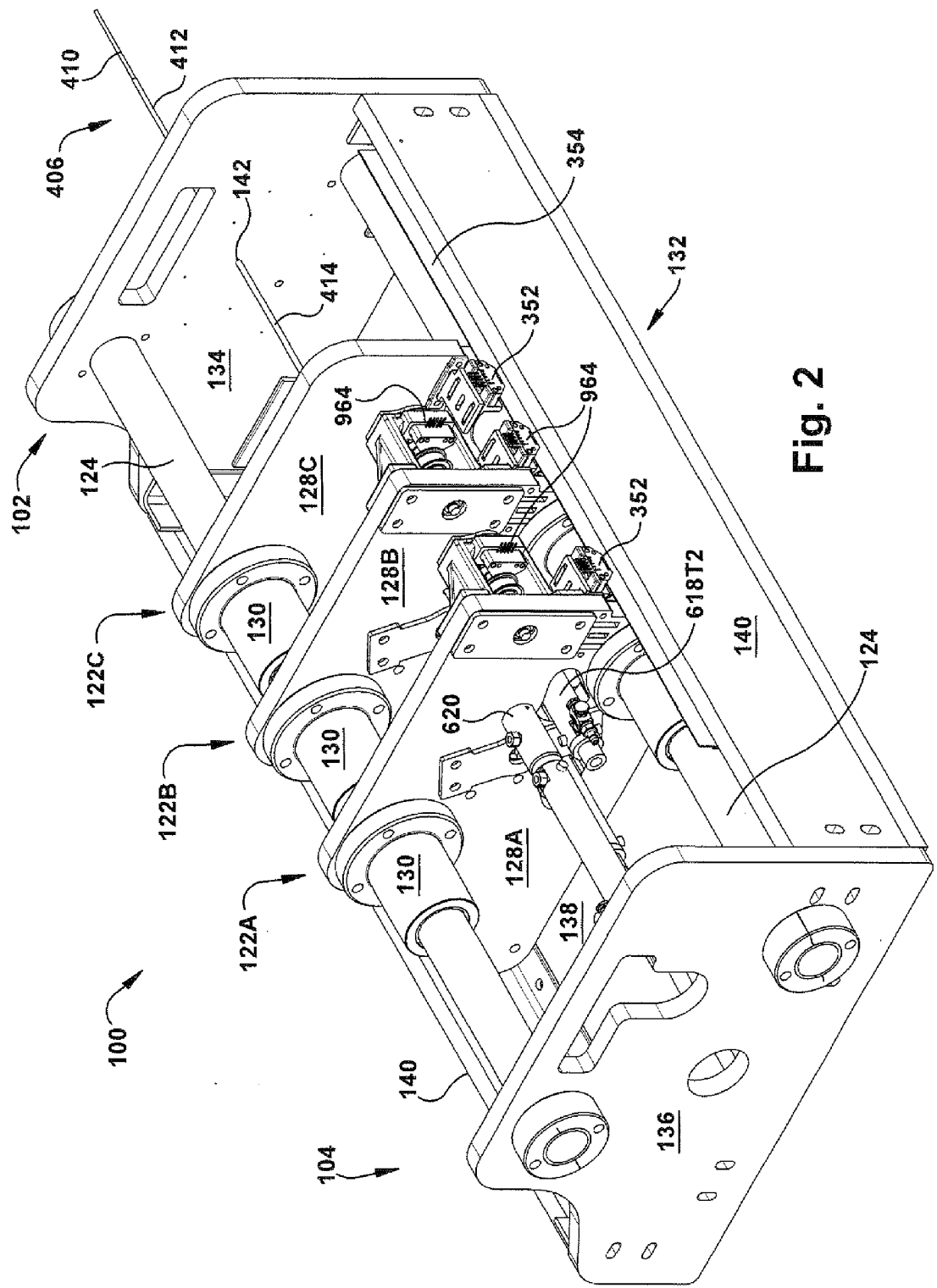
FIG. 2 is a perspective top view of the embodiment of FIG. 1, taken from the opposite side as FIG. 1.
Figure 3:
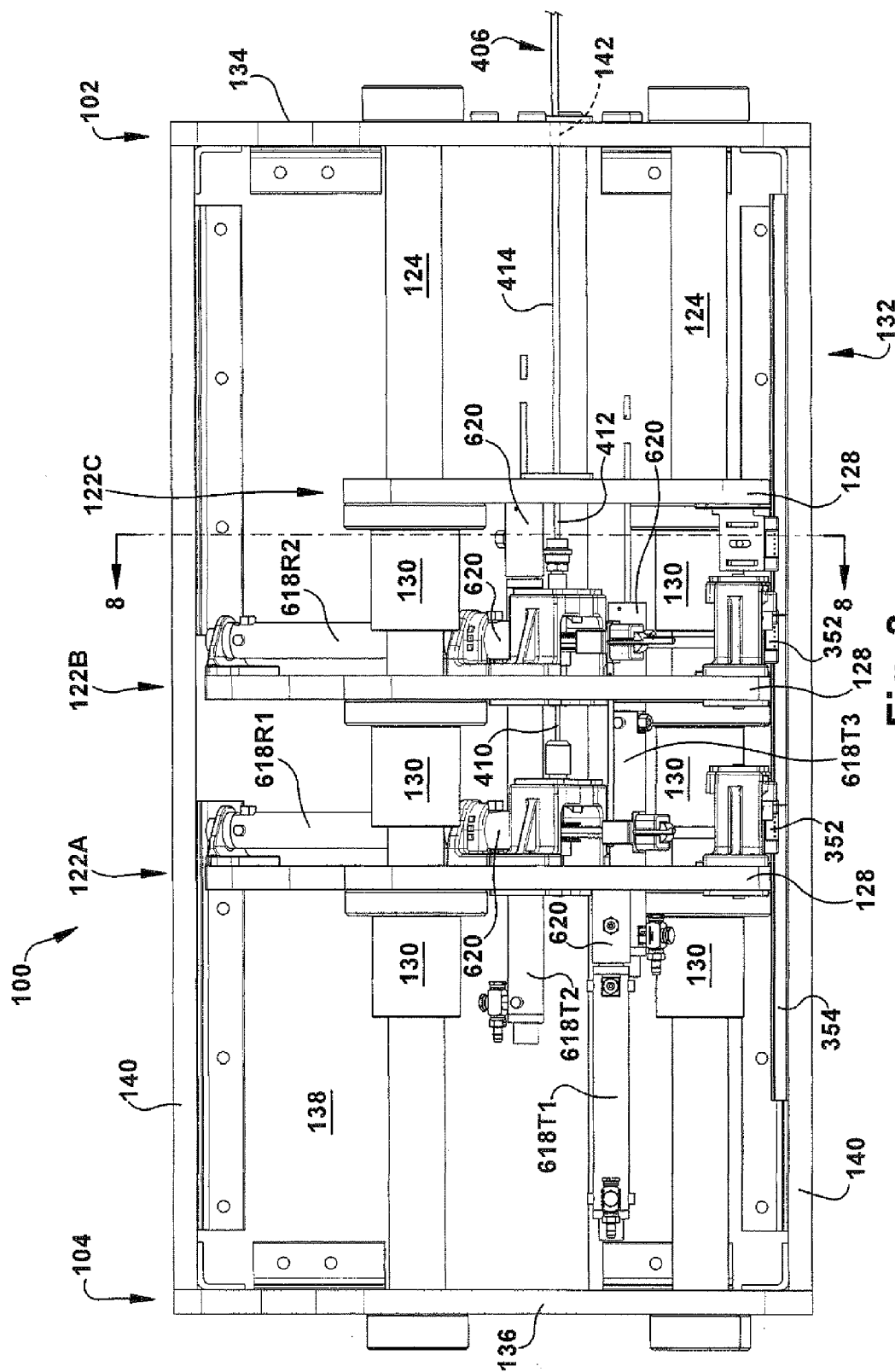
FIG. 3 is a top view of the embodiment of FIG. 1.

In accordance with the present invention, FIGS. 1-3 depict a multiple degree of freedom robot 100 intended for precision manipulation during MRI-guided intervention. FIG. 1 is a top perspective view showing the front 102 of the robot 100. FIG. 2 is a top perspective view showing the back 104 of the robot. FIG. 3 is a top (plan) view of the robot 100. The robot 100 depicted and described herein is a non-limiting example of a motive device for use in providing motive power to at least one moved structure in a magnetically-sensitive environment. The MRI-guided intervention use environment is a non-limiting example of a magnetically-sensitive environment.

The robot 100 will not distort the image acquired by the MRI machine, it can actively move under real-time computer control while the MRI machine is imaging, and it can be controlled with submillimetric precision. As such, the robot 100 is a nonmagnetic, MRI-compatible device that is actuated with nonmagnetic actuators. In order to facilitate the MRI-compatibility, the robot 100 is made using non-ferromagnetic materials such as, but not limited to, glass, acrylic, nylon, PEEK, acetal, ABS, ceramics, polycarbonate, silicone, other rubbers, other plastics, carbon fiber, fiberglass, brass, aluminum, graphite, a small amount of integrated encoder electronics, and the like.

The term "non-ferromagnetic" is used herein to indicate a material, and/or a quantity thereof, that does not cause significant unwanted effects (e.g., image artifacts, geometric distortion, heating of components, projectile/missile effects, or any other adverse consequences sufficient to affect the ability to obtain usable images) when used in an MRI environment. It is contemplated that a particular MRI technology or individual device may tolerate small amounts of certain materials which themselves are not, strictly speaking, entirely free of metallic/ferromagnetic content, and that different MRI technologies or devices may have higher or lower tolerances in this respect. It is therefore contemplated that some trace ferromagnetic material may be present, intentionally or not (e.g., as part of a control circuit or as metal filings/dust statically clinging to the robot 100), without destroying the "non-ferromagnetic" nature of a particular device as described herein. In other words, the non-ferromagnetic property of a particular robot 100 or material discussed herein is judged based on the lack of substantial or significant effects upon the MRI technology being used rather than a strict binary presence/absence standard for a particular kind and/or quantity of ferromagnetic material. However, for most use applications of the present invention, the robot 100 will be constructed substantially, and in most cases entirely, of materials that are non-ferromagnetic.

In addition, for most use environments of the present invention, the robot 100 will be at least partially powered non-ferromagnetically. Indeed, when the robot 100 is in a magnetically sensitive environment (e.g., in/near an MRI machine during imaging), the robot may be entirely powered non-ferromagnetically. An example of non-ferromagnetic power is fluidic power, such as, but not limited to, pneumatic (air) and/or hydraulic (oil) power. Different considerations may drive the selection of pneumatic versus hydraulic power for a particular use environment. For example, in a hospital setting, pneumatic pressure may be commonly and cleanly available via air lines running through the facility, while a source of hydraulic pressure may be difficult to obtain/ maintain cleanly in such a health care environment. Accordingly, the robot 100, or components thereof, could be designed to operate pneumatically using common pressure ranges built into hospital facilities. For example, air pressure ranges including, but not limited to, 20-25 psi (pounds per square inch), 40-50 psi, 70-80 psi, and 150-200 psi could be suitable for different use environments of the present invention. For hospitals having air lines providing pressurized air at about 50 psi, for example, it is contemplated that the robot 100, or components thereof, may be designed to be powered by pneumatic pressure of 50 psi or less.

The robot 100 may be useful to steer an active cannula 406, shown in FIGS. 4-5, for percutaneous interventions. A non-limiting example for a potential use environment for the robot 100 is in steering the active cannula 406 for minimally invasive ablation of the hippocampus with an end effector 408 which has ablative features. This particular procedure could be used to help treat temporal lobe epilepsy and offer a viable alternative to hippocampal lobectomy by resection.

With further reference to FIGS. 4-5, the active cannula 406 includes innermost, middle, and outermost concentrically nested tubes 410, 412, and 414, respectively, which can be more generally characterized as first, second, and third moved structures, respectively. As shown in FIG. 4, the innermost, middle, and outermost tubes 410, 412, and 414 may collectively define a longitudinal tube axis 416.

While the robot 100 is designed to steer an active cannula 406 comprising three concentric tubes 410, 412, and 414, the modular design allows for additional tubes to be added or subtracted. The term "tube" is used herein to reference the active cannula 406 use environment, but any suitable moved structure could be used without harm to the present invention. For example, adjacent (non-concentric) catheters could be individually moved within separate lumens of an insertion sheath by the robot 100. Generally speaking, the robot 100 can translate and/or rotate any desired items, having any or no relationship to each other, for any desired purpose. The active cannula 406 may carry, guide, or otherwise direct the placement of an end effector 408 having any desired observational or interactive function to a desired location within a patient's body for any desired reasons, interventional or otherwise. However, the use environment of a hippocampus and an end effector 408 of an ablative device will be used herein by way of example, for ease of description.

The robot 100 depicted in the Figures has five degrees of freedom, summarized by the arrows in FIG. 4, that do the following:
- translates the outermost tube 414, a relatively rigid titanium tube
- translates and rotates the middle tube 412, a precurved, superelastic Nitinol tube. The precurvature of the middle tube 412 may be customized to the geometry of the patient's hippocampus, for example, when the active cannula 406 is being used in a hippocampus ablation intervention. The middle tube 412 may nest directly inside the outermost tube 414.
- translates and rotates the innermost tube 410, a non-precurved, superelastic Nitinol tube. This innermost tube 410 may nest directly inside the middle tube 412. The ablating element (AKA "end effector" 408) and its catheter may be fixed to the innermost tube 410 and translate and rotate along with that innermost tube.

Figure 6:
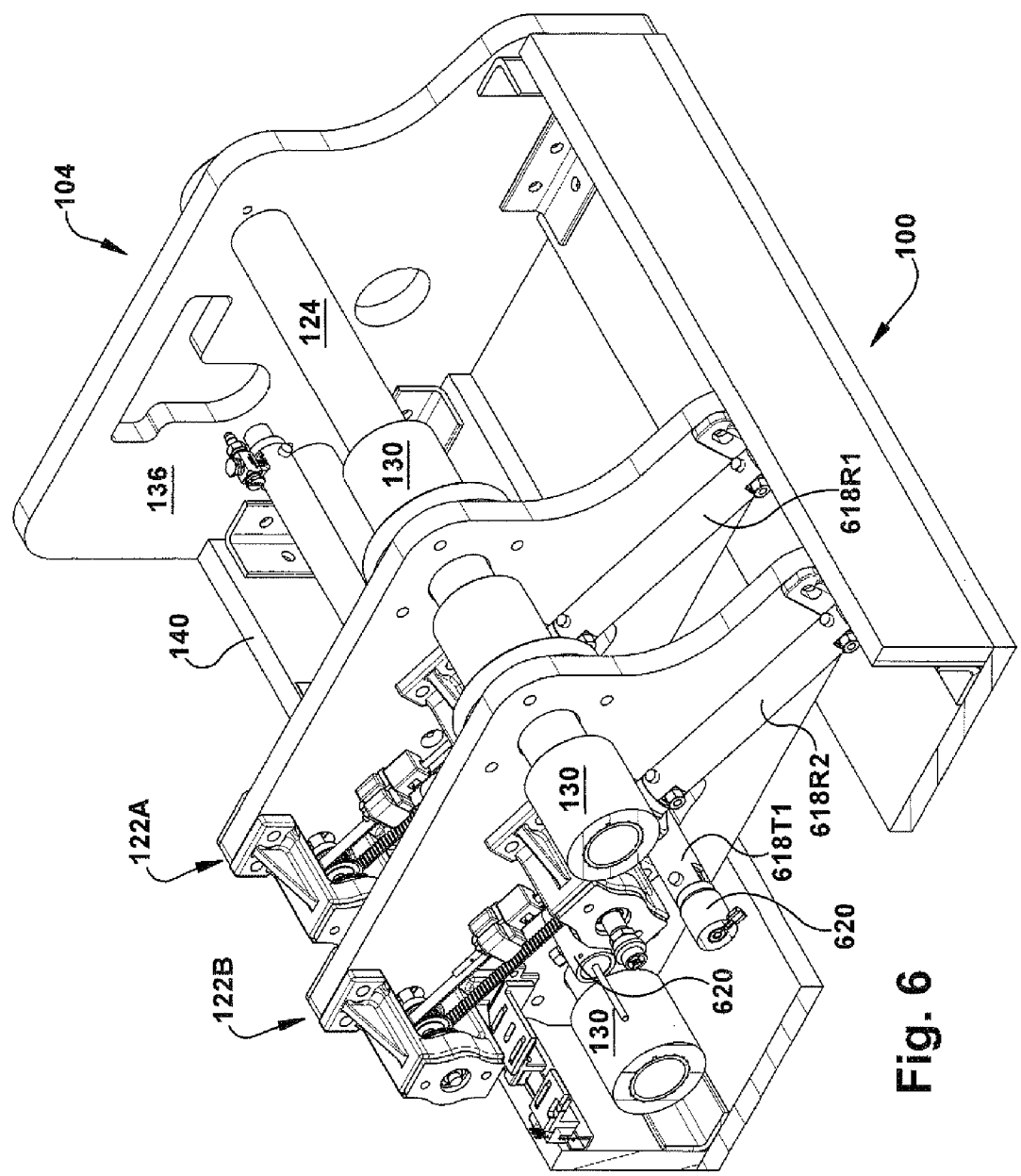
FIG. 6 is a partial perspective top view of the embodiment of FIG. 1.

Each degree of freedom described above may be driven by a non-ferromagnetic and/or nonferrometallic actuator, such as a fluidic actuator and, more particularly, such as the depicted pneumatic actuators 618, shown in example positions in FIG. 6, a partial perspective view of the robot 100.

An example of actuators 618 that can be used are pneumatic piston-cylinders manufactured by Airpot Corp of Norwalk, Conn. (e.g., their model Airpel E9 nonmagnetic) and are made using glass cylinders, graphite pistons, brass rods, and plastic components, so are entirely non-ferromagnetic. Other types of linear or rotary non-ferromagnetic actuators 618 could be additionally or alternatively developed for use with a particular robot 100 design, as well. The robot 100 may include one or more nonmagnetic rod locks 620 (e.g., air brakes) to prevent actuator 618 movement in the event of malfunction and/or if isolating the movement of one or more actuators is desirable for a particular use application of the robot. Alternative pneumatic actuators 618 could also or instead themselves include a "fail-safe" mechanism for "locking" the actuator from further movement without the use of such a supplementary rod lock 620.

Pneumatic lines (not shown) may be connected to the actuators with brass barbed fittings. The barbed fittings thread onto swivel, T-shape brass ports, providing 360° (three hundred sixty degrees) of adjustability for the direction of the incoming pneumatic line. The pneumatic lines connect the piston-cylinder actuators 618 to valves and pressure transducers that may not be MRI-compatible and, in such case, the pneumatic lines should be long enough to permit the MRI-incompatible portions of the motive device and its power system to be located sufficiently far away from the MRI machine to avoid adverse effects.

With reference back to FIGS. 1-3, the robot 100 design is modular in that several modules 122 translate along at least one guiding rail, such as the depicted pair of guide rods 124, with each module 122 being associated with at least one tube 410, 412, 414 of the active cannula 406. The guide rods 124 pictured are made at least partially from carbon fiber but could also or instead include high rigidity plastics or any other suitable materials. The number of modules 122 may be equal to the number of concentric tubes 410, 412, 414 composing the active cannula 406. The base for a single module 122 is a plate 128, such as a plastic plate, that translates via one or more linear bearings 128 which ride along the guide rods 124. The bearings 128 shown in the Figures are plain linear type but alternatively could be recirculating ball type or any other suitable type. Components for the module 122, such as a linear-to-rotary transmission and/or optical encoder reader as will be described below, may be mounted to the plate 128, as shown in the Figures.

More specifically, the guide rods 124 are shown in the Figures as being supported by a rigid, box frame 132. The frame has two supporting plates, a front supporting plate 134 and a rear supporting plate 136. The guide rods 124 extend longitudinally between these front and rear supporting plates 134 and 136 and are supported thereby, such as via the use of one-piece shaft collars mounted on the front and rear supporting plates. The front and rear supporting plates 134 and 136 may be further joined together to form the frame 132 by one or more bottom plates 138 (two shown) and/or one or more side plates 140 (two shown). The resulting box frame may provide a structure used for the mounting and proper alignment of the linear transmissive strip as well as for the mounting of fiducials for image registration. In use, the frame 132 sits (external to the patient's skull) on the bed of the MRI machine. Alternatively, the frame 132 could be mounted on a movable carrier or bracket (not shown), which functions to adjust the direction of initial active cannula 406 insertion to desired pitch and yaw angles; adjustment could be manual or use any desired number of additional actuators 618 or other adjustment aids. Whether or not a carrier or bracket is provided, the frame 132 and any other elements of the motive device or its associated structures which are intended for use within or sufficiently near to an MRI machine to interact with the magnetic field should be constructed at least partially, and in most cases entirely, of non-ferromagnetic materials.

Optionally, due to the limited space envelopes in and near an MRI machine, the frame 132 or other components of the robot 100 could be designed for placement and/or operation within certain predefined size and/or shape limits which affect the physical configuration of the robot. For example, and particularly if it is desired for one or more of the tubes 410, 412, 414 to translate along a substantially curvilinear (including purely curved) path for a particular use environment of the present invention, the guide rods 124 for that robot 100 could include a curvilinear profile, corresponding substantially to the desired translation path, to guide translational motion of an associated module 122. It is also contemplated that a single robot 100 could include multiple guide rods 124, each corresponding to a different desired translational path for an associated module 122 of a plurality of modules of that single robot.

Referring more specifically to the modules 122, at least one module is supported by the guide rods 124, is located longitudinally between the front and rear supporting plates 134 and 136, and is configured to provide at least one of translational and rotational motion to a moved structure, such as a tube 410, 412, 414 of an active cannula 408. In the configuration shown in the Figures, the moved structure extends from the module 122 longitudinally toward and beyond (such as through cannula aperture 142) the front supporting plate 134. The translational motion of the moved structure, when present, is provided by motion of the module 122 between the front and rear supporting plates 134 and 136, longitudinally along and guided by one or more guide rods 124.

For magnetically sensitive use environments of the present invention, such as during MRI imaging, the module 122 providing the translational and/or rotational motions to the moved structure may do so entirely via a non-ferromagnetic power source, such as pneumatics. Additionally, the module 122 in such magnetically sensitive use environments may be made entirely from non-ferromagnetic materials.

With specific reference to the robot 100 depicted in FIGS. 1-3, a first module 122A is configured to provide both translational and rotational motions to a first moved structure, hereafter referenced as innermost tube 410. The first module 122A includes a pneumatic first translational actuator 618T1 for translating a first plate 128A attached to the innermost tube 410 along the guide rods 124. The first module 122A also includes a pneumatic first rotational actuator 618R1 for rotating the innermost tube 410 with respect to the first plate 128A;

A second module 122B is configured to provide both translational and rotational motions to a second moved structure, hereafter referenced as middle tube 412. The second module 122B includes a pneumatic second translational actuator 618T2 for translating a second plate 128B attached to the middle tube 412 along the guide rods 124. The second module 122B also includes a pneumatic second rotational actuator 618R2 for rotating the middle tube 412 with respect to the second plate 128B;

A third module 122C is configured to provide translational motion, without rotational motion (as desired for the active cannula 406 ablation example being used herein) to a third moved structure, hereafter referenced as outermost tube 414. The third module 122C includes a pneumatic third translational actuator 618T3 for translating a third plate 128C attached to the outermost tube 414 along the guide rods 124.

In keeping with the desire to make the robot 100 shown in the Figures MRI-compatible, the structures comprising the first, second, and third modules 122A, 122B, and 122C may all be made entirely from non-ferromagnetic materials.

Kinematics of the robot 100 design are such that each actuator 618 may independently control the translation or rotation of one of the tubes 410, 412, 414 with respect to the others. Furthermore, a feature of the robot 100 kinematics is that actuators 618 directly control the relative linear position between the first and second modules and between the second and third modules, so that movement of these modules relative to one another may be controlled precisely. Stated differently, the translational actuator 618T3 of the third module 122C extends between the front supporting plate 134 and the third plate 128C, the translational actuator 618T2 of the second module 122B extends between the third plate 128C and the second plate 128B, and the translational actuator 618T1 of the first module 122A extends between the second plate 128B and the first plate 128A. Because each module 122 translates relative to an adjacent structure, the piston rods of the translational actuators 618T1, 618T2, 618T3, can be relatively short—and thus avoid undue beam-bending effects-as compared to an alternate situation (not shown) in which each module is pushed or pulled by an actuator extending between that module and a common ground surface (e.g., the front supporting plate 134). In the depicted arrangement, as opposed to the immediately aforementioned alternate situation, all of the translational actuators 618T1, 618T2, 618T3 may have substantially the same design, thus reducing the number of separate parts that must be stocked/provided for fabrication or repair.

Each tube 410, 412, 414 undergoing translation only may be rigidly fixed to its respective module 122A, 122B, 122C and may pass through (preferably in a relatively nonfrictional/sliding manner) an aperture in the module(s) aligned axially with the cannula aperture 142. Each tube 410, 412, 414 undergoing both translation and rotation may be clamped to a thick-walled shaft (944, shown in FIG. 9) that is aligned axially with the cannula aperture 142 and that is mounted by several components to that tube's respective module 122A, 122B, 122C, as will be discussed below. The head of the piston-cylinder of the actuator 618 responsible for relative translation of a chosen module 122A, 122B, 122C may be rigidly fixed to the module base plate 128A, 128B, 128C. The piston rod of the same actuator 618 may be flexibly coupled to the base plate 128A, 128B, 128C of the module 122A, 122B, 122C directly preceding, in operative sequence, the chosen module 122A, 122B, 122C. The directly preceding module 122A, 122B, 122C carries another tube 410, 412, 414 to be inserted into the patient directly prior to the smaller, subsequent tube 410, 412, 414.

In other words, the outermost tube 414 is carried by the frontmost module 122C. The middle tube 412 is carried by the middle/intermediate module 122B. The innermost tube 410 is carried by the aftmost module 122A. The nesting of the tubes 410, 412, 414, when operatively coupled to the robot 100, is shown in FIGS. 1-3. A portion of the innermost tube 410 located on a "forward" side of the aftmost module 122A (i.e., a side of that module opposite the rear supporting plate 136) may be substantially located within the lumens of both the middle and outermost tubes 412 and 414. A portion of the middle tube 412 located on a "forward" side of the middle module 122B (i.e., a side of that module opposite the rear supporting plate 136) may be substantially located within the lumen of the outermost tube 414.

The modules 122A, 122B, 122C are designed to compactly collapse together as the active cannula 406 is inserted into the patient or other robot work space. As the middle and aftmost modules 122B and 122A translate forward, the piston-cylinder of the actuator 618T3 translating the frontmost module 122C passes through clearance holes in the middle and aftmost modules 122B and 122A. Similarly, the piston-cylinder of the actuator 618T2 translating the middle module 122B passes through a clearance hole in the aftmost module 122A.

Figure 7:
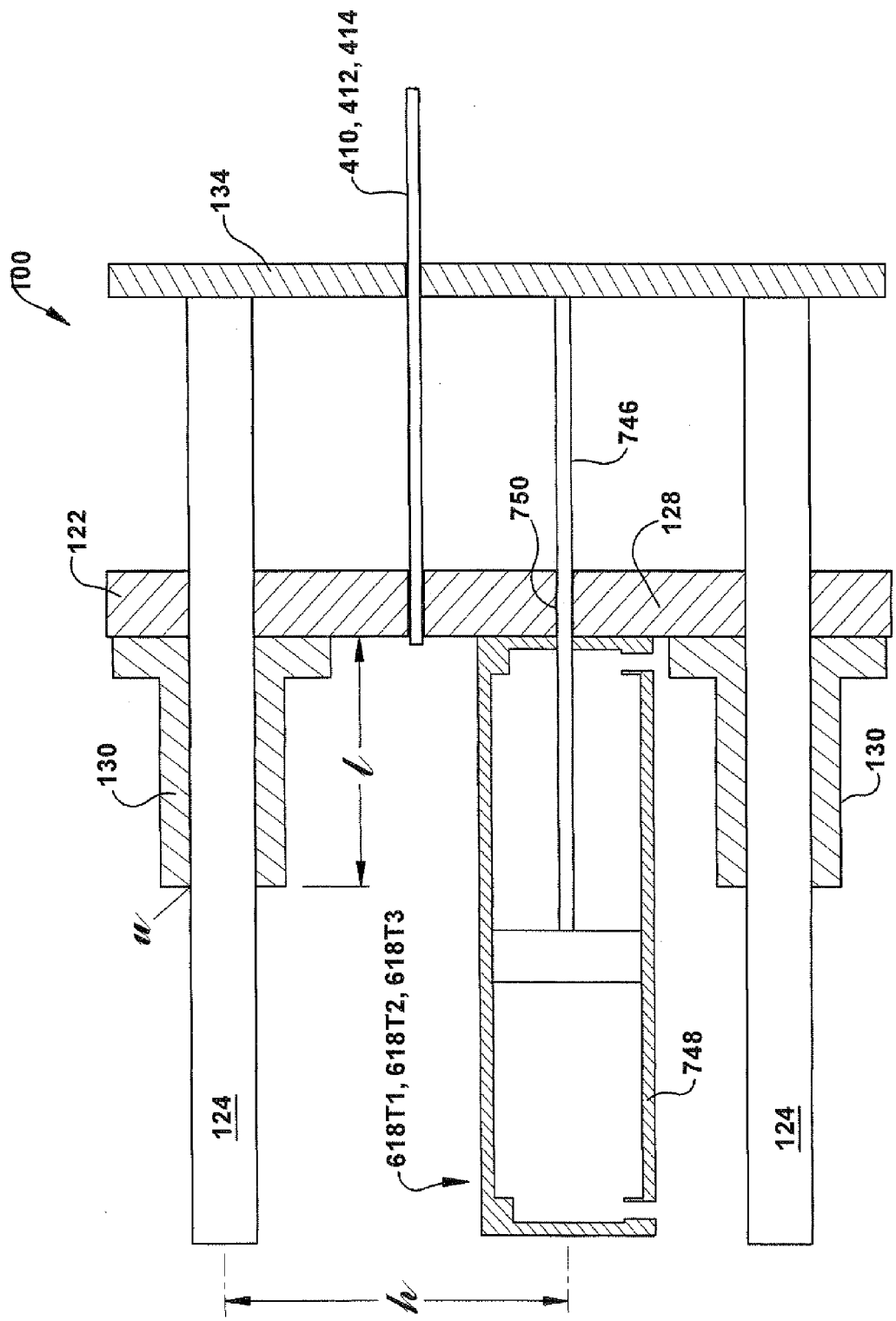
FIG. 7 is a partial schematic view of a component of the embodiment of FIG. 1.

FIG. 7 depicts schematically a top view of one suitable scheme for managing the translational motion of a module 122, and thus the associated tube 410, 412, 414, with respect to the guide rods 124. In FIG. 7, the module 122 has an attached tube 410, 412, 414 and includes a translational actuator 618T1, 618T2, 618T3. At least one linear bearing 130 (two shown) is used to slidably couple the plate 128 to the guide rods 124. A piston rod 746 of the translational actuator 618T1, 618T2, 618T3 is coupled to the front supporting plate 124 and a corresponding cylinder 748 is coupled to the plate 128 so that extension or retraction of the translational actuator moves the module 122 (and thus the associated tube 410, 412, 414) via translation longitudinally with respect to the frame 132.

Binding/sticking of the linear bearings 130 against the guide rods 124 can be avoided/prevented by configuring the bearings with a length "l" which is directly proportional to the distance "h" between the actuator 618T1, 618T2, 618T3 and a central axis of the guide rod and to the frictional coefficient "µ" between the bearing and the guide rod, using a ratio such as:

$$l = 2\mu h$$

Linear position sensing may be accomplished via one or more optical linear encoders 352 and at least one transmissive linear strip 354. The number of linear encoders 352 provided to the robot 100 may be equal to the number of modules 122 (which, in turn, may be equal to the number of tubes 410, 412, 414 being rotated and/or translated by the robot 100 during the intervention). One linear encoder 352 may be mounted to each module 122 for sensing the absolute linear position of the module 122. Reading off one common transmissive strip 354 with index, the linear encoders 352 output digital signals to a data acquisition device. The index provides a zero position, such that the encoder counts reset to zero when the encoder slides past the index position on the transmissive strip. The linear strip 354 may be mounted on one side of the robot 100 frame, or in any other desired position. Through use of sufficiently precise linear position sensing, the absolute and relative positions of the modules 122, and thus their associated tubes 410, 412, 414 can be determined with a desired degree of accuracy. This position information may then be used, for example, to control relatively sensitive actuators 216 to achieve a desired surgical/intervention result for the patient.

Figure 8:
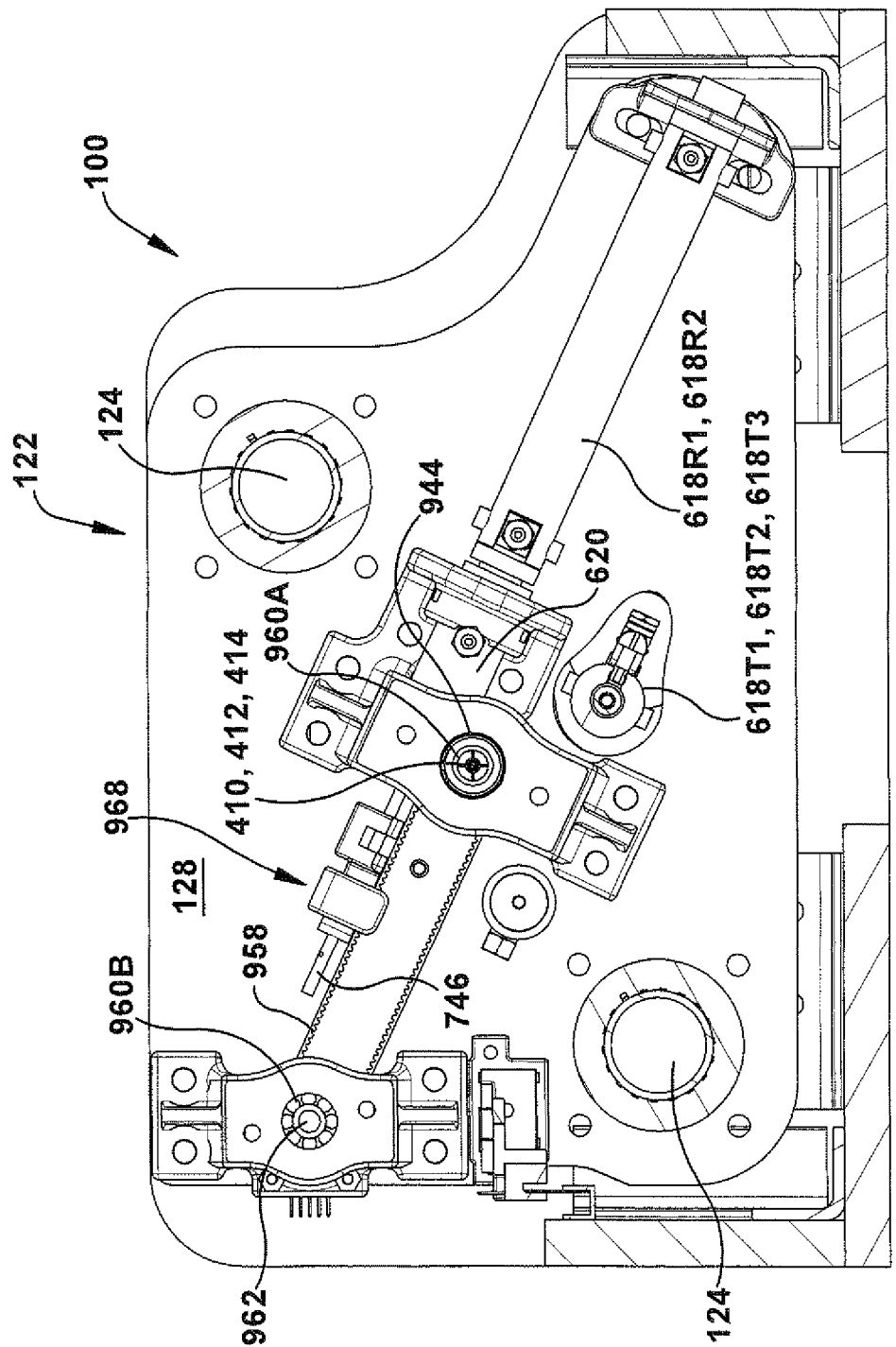
FIG. 8 is a cross-sectional view taken along line 8-8 of FIG. 3.
Figure 9:
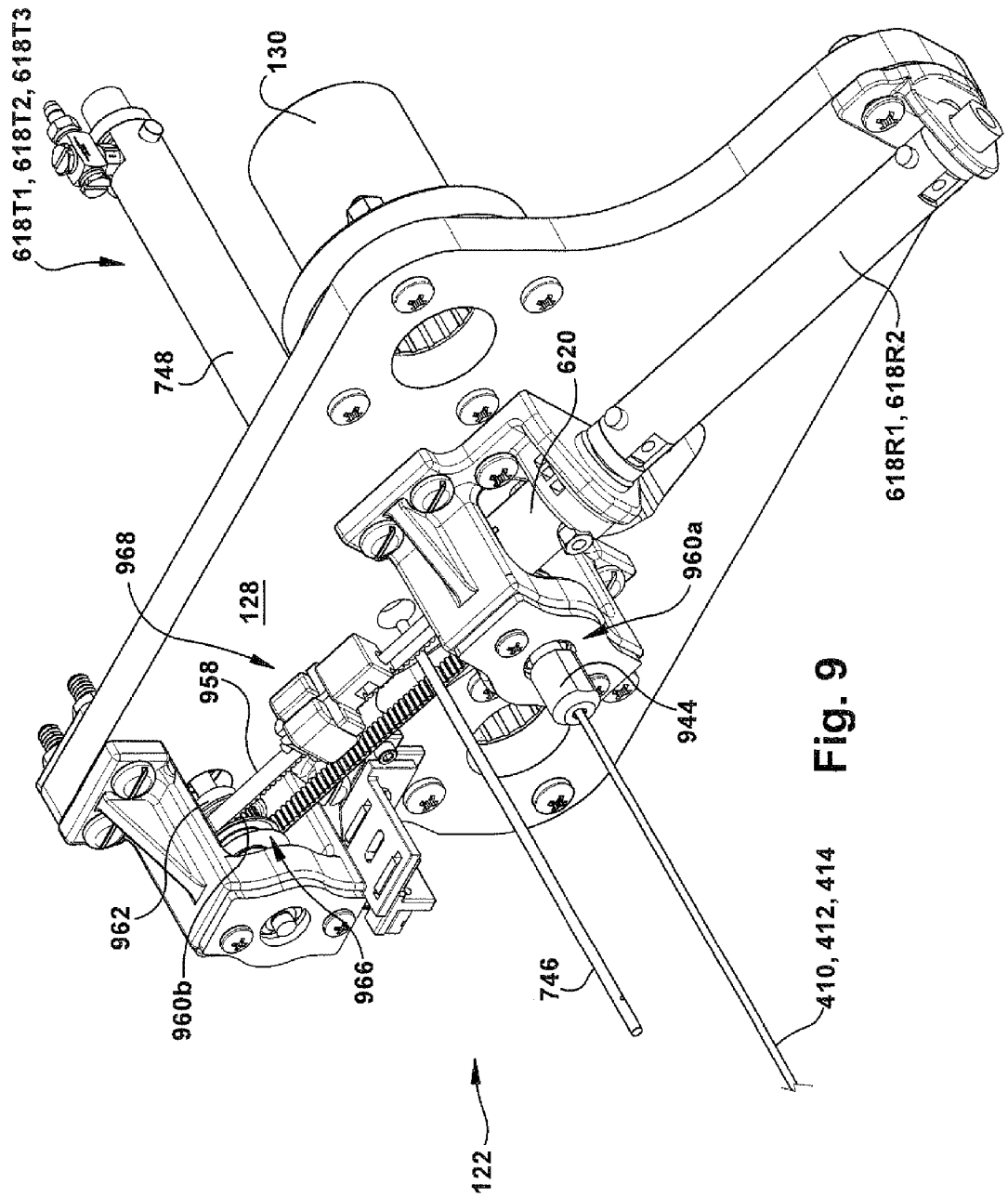
FIG. 9 is a partial perspective top view of a component of the embodiment of FIG. 1.
Figure 10:
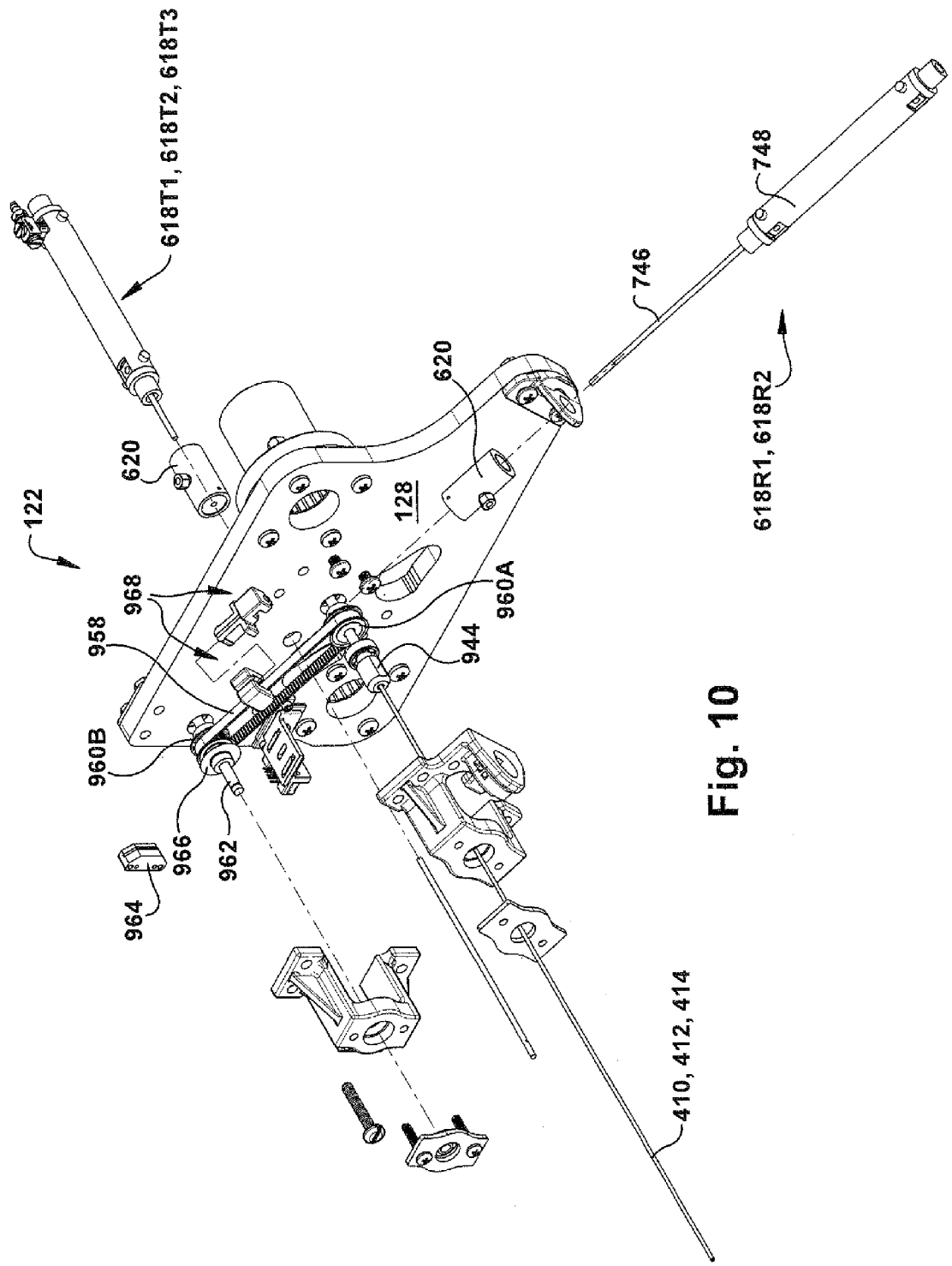
FIG. 10 is an exploded perspective top view of the component of FIG. 9.

Turning to FIGS. 8-10, depicting the rotation mechanisms of a single module 122, each tube 410, 412, 414 to be rotated may be moved by a rotational actuator 618R1, 618R2 including a linear-to-rotary transmission mechanism 956 converting translation of a linear actuator to rotation of the shaft 944 to which the tube is clamped. The rotational actuators 618 could also or instead include at least one pure rotary actuating/motive device (not shown), of any suitable type, such as a rotary actuator, stepper motor, or other suitable device, powered pneumatically, hydraulically, electrically, or in any other desired way.

In the linear-to-rotary arrangement shown in the Figures, however, the transmission mechanism 956 may include a timing belt 958 stretched relatively tautly between two pulleys 960. The pulley 960A located closer to the rotational actuator 618R1, 618R2 is supported by the thick-walled first shaft 944 holding the clamped tube 410, 412, 414. The second pulley 960B is supported by a second shaft 962, which also may carry a transmissive disc 966 with an indexing feature for sensing the angular position of the tube 410, 412, 414 being rotated. An optical rotary encoder 964 may read the disc position and output a corresponding digital signal to a data acquisition device. Additionally or alternatively, a ratchet/pawl or other sensing arrangement (not shown) could index to the ribbed inner surface of the timing belt 958 to closely monitor the rotational position of the shaft 944 and thus the tube 410, 412, 414 rigidly attached thereto.

The translation-to-rotation transmission mechanism 956 could have alternative designs to that discussed above and shown in the Figures. A non-limiting example of another suitable transmission mechanism 956 design which may have compactness and reliability advantages in some use environments uses two ratcheting gears, both mounted to the thick-walled first shaft 944 with a clamped tube. The gears ratchet in opposite directions; each is driven by a pawl mounted to the piston rod of a pneumatic actuator 618. A belt clamp 968 may couple the timing belt 958 to the piston rod 746 of the rotational actuator 618R1, 618R2. Both the first and second shafts 944, 962 may be supported by bearings, which may be ball-type but alternatively or additionally could be journal-type, roller-type, or any other suitable type of bearing. The timing belt clamp 968 may include two parts. One part of the timing belt clamp may have a loose fit hole at one end and a flexible barb at the other end. The piston rod 746 is inserted through the hole and is fastened with two plastic hex nuts. This coupling compensates for any present small axial misalignment of piston rod 746 and timing belt 958. The flexible barbed end snaps snugly inside the second part, and the timing belt 958 is clamped between the snapped parts. Actuation of the rotational actuator 618R1, 618R2 will, through action of the timing belt clamp 968, cause the timing belt 958 to travel around the pulleys 960, and, by extension, to rotate the shaft 944 and the tube 410, 412, 414 rigidly attached thereto about a desired degree of rotation relative to the tube axis 416. Optionally, at least one of the rotational actuators 618R1, 618R2 can, through sizing and selection of the component parts thereof, provide at least three hundred sixty degree (360°) rotation of the tube 410, 412, 414 in both counterclockwise and clockwise directions.

Figure 11:
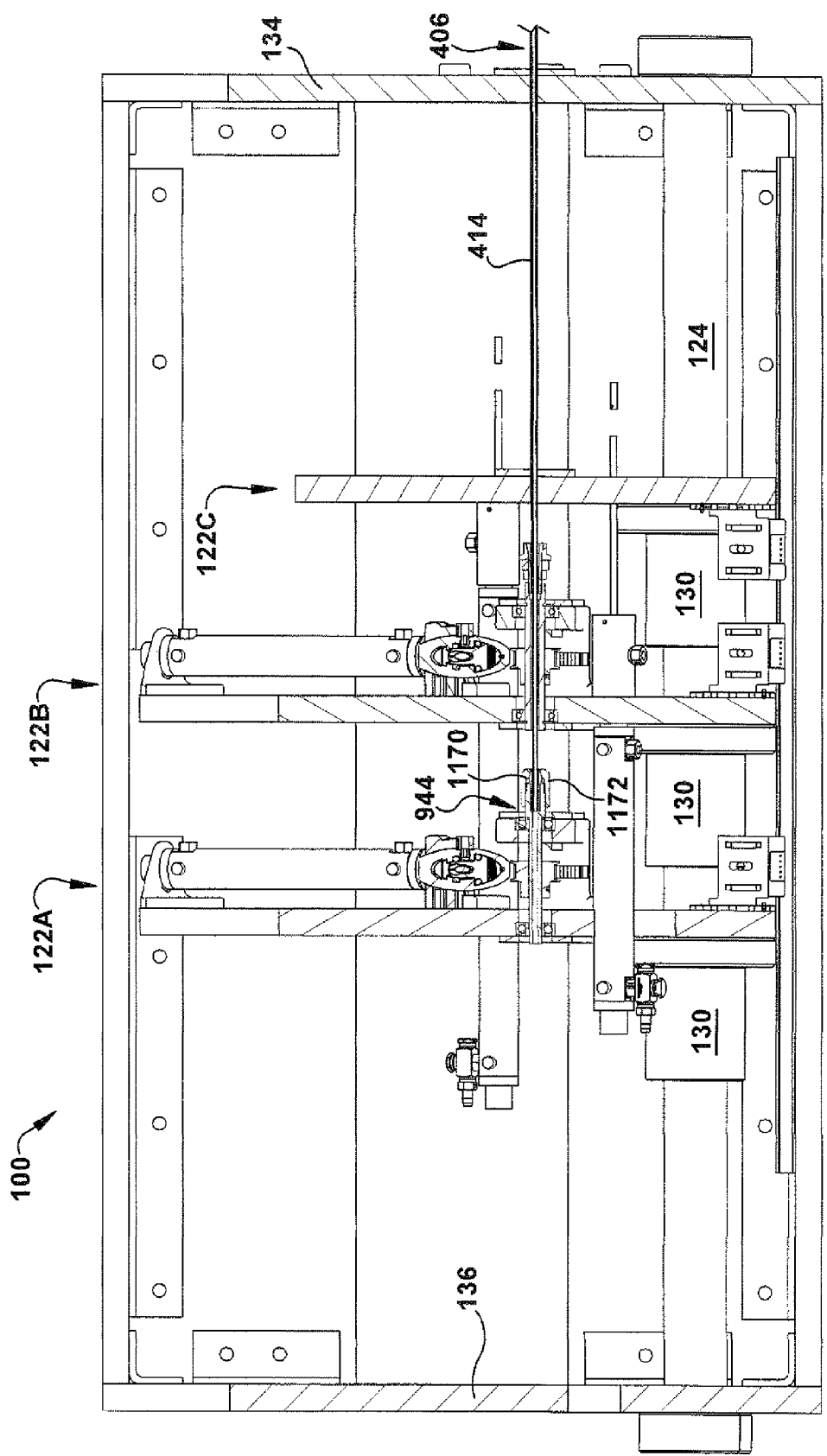
FIG. 11 is a cross-section taken along line 11-11 of FIG. 1.

Each rotating tube 410, 412, 414 may be clamped to a thick-walled first shaft 944 using, for example, an aluminum collet 1170 and a collet nut 1172, as shown in FIG. 11. The robot 100 depicted in the Figures includes may include different collet designs to accommodate smaller and larger tube outer diameters ("ODs"). One design, for smaller tube diameters, threads an aluminum collet nut onto external threads at the shank of the thick-walled first shaft 944. An aluminum collet 1070 mates to the beveled inner diameter of the shaft 944 and grips the rotating tube 410, 412, 414. The second, alternative design for larger tube diameters uses an aluminum collet 1070 with a threaded shank. This collet 1070 threads into the shank of the thick-walled first shaft 944. A collet nut threads in the opposite direction along the collet, clamping the tube 410, 412, 414 from the back side.

Each actuator 618 is shown in the Figures as being controlled by a 4-way proportional spool valve. Chamber pressures of the piston-cylinder could also or instead be regulated by pressure control valves. The controls architecture for one actuator 618 may use, for example, three pressure sensors and one optical encoder. The pressure sensors and/or valves, when present, may be housed inside a (ferromagnetically shielded) Faraday cage located at a distance of three to four meters from the bore of the MRI machine within the room housing the MRI machine, or may even be located in a separate room, which is ferromagnetically shielded from the room which houses the MRI machine. In this design, pneumatic lines of suitable length may run from the valves in the Faraday cage or separate room to the robot 100, to help direct pneumatic power from a compressor, air line, or other suitable pneumatic source to the robot. Digital encoder signals may be sent via shielded cables from the robot 100 to the data acquisition cards carried by a controller. The user interface may operate interactively through the controller. Engagement of the air brakes or rod locks may be controlled using a valve manifold of 5-port, 2-way valves, and/or using any other suitable control means or mechanism. This arrangement is shown schematically in FIG. 12.

Figure 12:
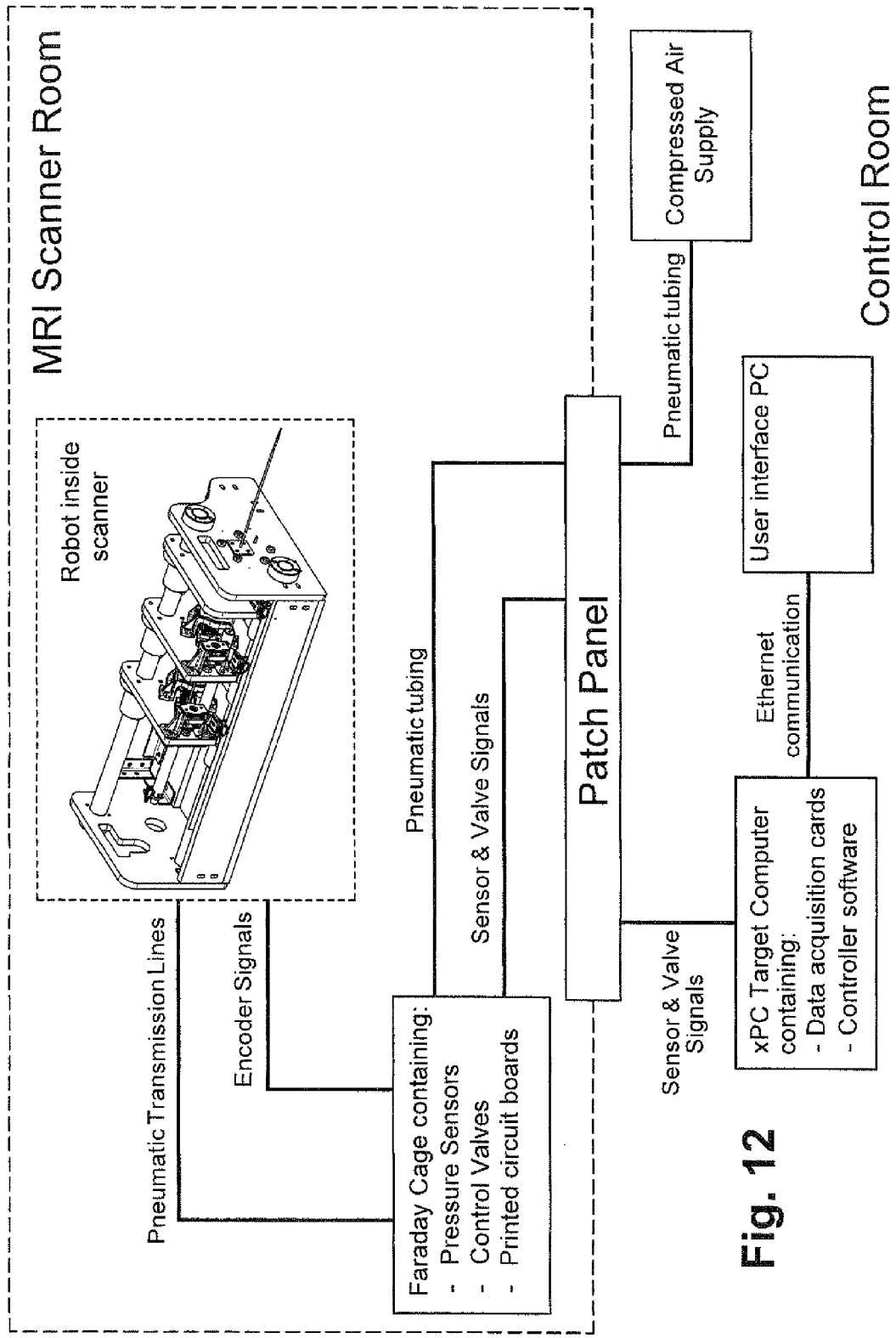
FIG. 12 is a schematic view of an example use environment for the embodiment of FIG. 1.

A nonlinear control algorithm for controlling the robot 100 may be used in high-precision position tracking using sliding mode control. Alternatively, the nonlinear control algorithm could implement an adaptive sliding mode controller. The controller may be implemented in software with MATLAB Simulink, from MathWorks of Natick, Mass., optionally using xPC Target (also from MathWorks) for real time computer control. Data acquisition cards may be housed inside the controller. The controls software could additionally or alternatively be implemented with C code and microcontrollers. The controller may be located in the MRI control room, inside the Faraday cage, or in any other suitable location(s). An Ethernet cable may facilitate communication between target and host machines. A shielded cable of any suitable type may transmit analog command signals between the target machine and the valves and sensors. FIG. 12 also includes a schematic view of one suitable example arrangement similar to the above.

Stated differently, translational and/or rotational motions of at least a chosen one of the innermost, middle, and outermost tubes can be controlled using equipment similar to that shown in FIG. 12. An endpoint position of a distal end of the chosen tube is obtained using image registration from an image obtained using an MRI machine. A desired new position for the distal end of the chosen tube is selected via a user interface. The inverse kinematics of the motive device are solved, such as by using an xPC target computer. A desired motion for translation and/or rotation of the tube is commanded to move the distal end of the chosen tube into the desired position. With a feedback control system, translation and/or rotation of the chosen tube is controlled in the desired motion. The feedback control system for the translation and/or rotation comprises a pressure sensor of the pneumatic supply line, a pressure sensor of the chambers of a pneumatic piston-cylinder operatively coupled to the module of the chosen tube, and a position sensor (e.g., an optical encoder, as previously described) for sensing the position of the module of the chosen tube with respect to a relatively stationary reference. The feedback control system can also include a four-way mass flow proportional control valve controllable by other portions of the feedback control system to selectively direct pneumatic pressure to at least one chamber of the pneumatic piston-cylinder, an air brake for selective actuation to prevent a change in pneumatic pressure of at least one chamber of the pneumatic piston-cylinder, and a plurality of elongated pneumatic lines fluidically interconnecting at least one chamber of the pneumatic piston-cylinder and at least one air brake to at least one ferromagnetic proportional control valve and at least one ferromagnetic brake control valve. The ferromagnetic pressure sensors and control valves should be located sufficiently far from the MRI machine to substantially prevent unwanted interference between the ferromagnetic pressure sensors and control valves and the MRI machine. A scanner room patch panel can be used to route control signals between the position sensor, pressure sensors, and control valves and a package of computer electronics located in a control room which is ferromagnetically shielded from the MRI machine. The computer electronics package includes an xPC target machine with data acquisition cards, a user interface PC, and an ethernet connection between the target machine and the user interface PC.

FIGS. 13A-13D schematically depict a simple sequence of operation of the robot 100 that uses three modules 122A, 122B, 122C to sequentially translate innermost, middle, and outermost tubes 410, 412, 414, respectively, along a longitudinal tube axis 416. The tubes 410, 412, 414 are shown as having already been operatively attached to their respective modules 122. It is presumed that power is being supplied to the robot 100 of FIGS. 13A-13D in any desired manner, to drive the desired actions. For example, if the robot 100 is to be powered entirely non-ferromagnetically, a system of suitable pneumatic sources, lines, valves, pressure sensors, and the like could be provided by one of ordinary skill in the art to supply motive power to the moving components of the robot for that particular use application of the present invention.

Figure 13A:
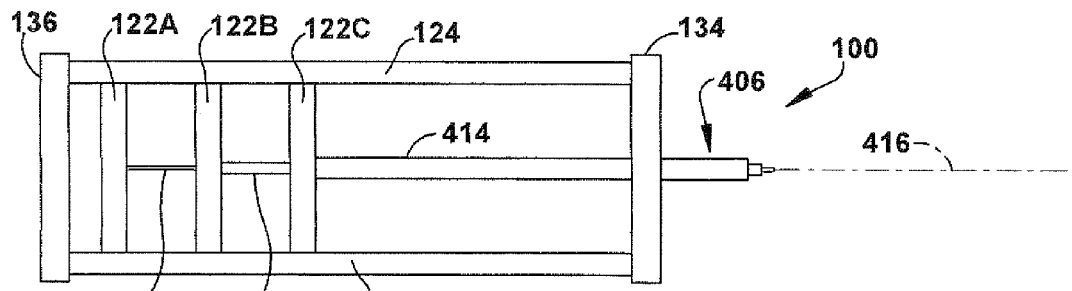
FIGS. 13A-13D schematically depict an example sequence of operation of the embodiment of FIG. 1.
Figure 13B:
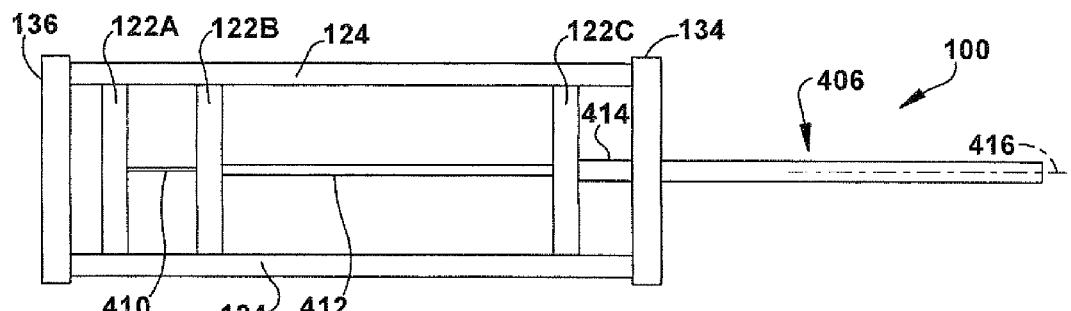
Figure 13C:
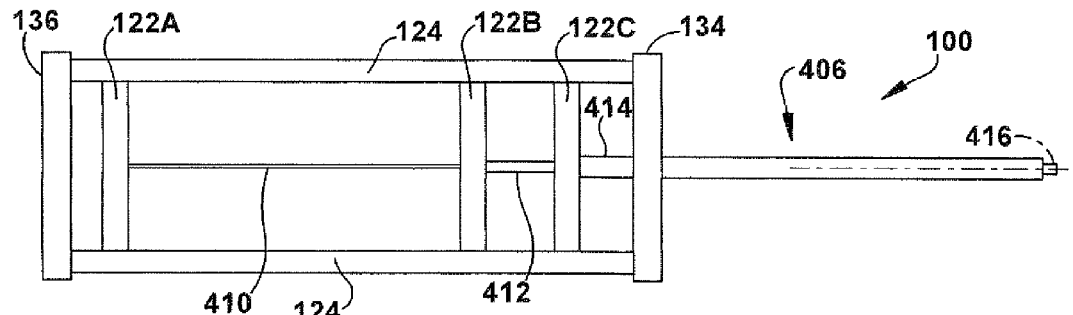
Figure 13D:
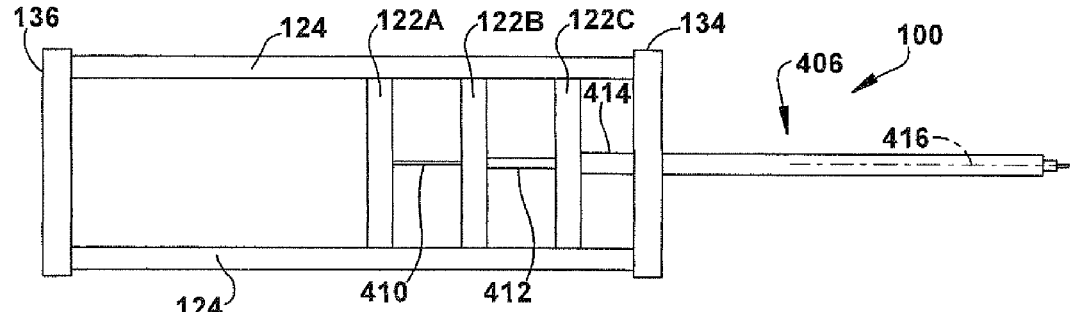

In FIG. 13A, all three modules 122A, 122B, 122C and their respective tubes 410, 412, 414 are substantially retracted. In FIG. 13B, translational actuator 618T3 has been applied to translate third/frontmost module 122C, and associated outermost tube 414, to a substantially extended position, where it remains in FIGS. 13C-13D. In FIG. 13C, translational actuator 618T2 has been applied to translate second/middle module 122B, and associated middle tube 412, to a substantially extended position, where it remains in FIG. 13D. In FIG. 13D, translational actuator 618T1 has been applied to translate first/aftmost module 122A, and associated innermost tube 410, to a substantially extended position. There may have also been rotation of one or more tubes 410, 412, 414 (optionally using rotational actuators 618R1, 618R2) during the translations shown in FIGS. 13A-13D. The sequence of FIGS. 13A-13D, or portions thereof, may be partially or fully performed at any speed/timing, in any direction (e.g., forward/backward), under any desired motive power, and in any desired manner to move and/or steer the moved structure(s) (such as an active cannula 406 or any components thereof) for a particular use environment of the present invention, and one of ordinary skill in the art could readily design a robot 100 to perform a suitable task as desired.

In many use environments of the present invention, the rotational and/or translational actuators 618T1, 618Y2, 618T3, 618R1, 618R2 may be provided at a sufficiently small scale to allow highly precise and minuscule incremental motions of the actuator-driven structures. For example, translation resolutions on the order of 0.006 millimeters and/or rotation resolutions on the order of 0.3 degrees may be achieved in a predictable and repeatable manner using particularly chosen pneumatic actuators. The robot 100 can thus facilitate accurate surgeries/interventions which can be carried out in a magnetically sensitive environment, such as during MRI imaging.

While aspects of the present invention have been particularly shown and described with reference to the preferred embodiment above, it will be understood by those of ordinary skill in the art that various additional embodiments may be contemplated without departing from the spirit and scope of the present invention. For example, alternative layouts of the robot 100 system (from that shown in the Figures) inside the MRI machine room and control room(s) are possible, and rearrangements of system components may occur during integration of the robot 100 system with other operating room equipment. The specific methods described above for using the robot 100 are merely illustrative; one of ordinary skill in the art could readily determine any number of tools, sequences of steps, or other means/options for placing the above-described apparatus, or components thereof, into positions substantively similar to those shown and described herein. Any of the described structures and components could be integrally formed as a single piece or made up of separate sub-components, with either of these formations involving any suitable stock or bespoke components and/or any suitable material or combinations of materials. Though certain components described herein are shown as having specific geometric shapes, all structures of the present invention may have any suitable shapes, sizes, configurations, relative relationships, cross-sectional areas, or any other physical characteristics as desirable for a particular application of the present invention. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. A motive device for use in magnetically sensitive environments, the motive device comprising:
    a front supporting plate;
    a rear supporting plate;
    at least one guiding rail extending longitudinally between the front and rear supporting plates and supported thereby; and
    at least one module supported by direct contact with the at least one guiding rail, the at least one module being located longitudinally between the front and rear supporting plates, and configured to provide both translational and rotational motions to a moved structure extending from the at least one module longitudinally toward and beyond the front supporting plate, the translational motion guided by motion of the at least one module between the front and rear supporting plates longitudinally along the at least one guiding rail, translational motion of the moved structure being guided by concurrent and proportional translational motion of the at least one module between front and rear supporting plates which are relatively stationary with respect to the moved structure and the at least one module, the at least one module providing the at least one of translational and rotational motions to the moved structure entirely pneumatically;
    wherein the motive device is made entirely from non-ferromagnetic materials.

2. The motive device of claim 1, comprising:
    a first module configured to provide both translational and rotational motions to a first moved structure, the first module including a pneumatic first translational actuator for translating a first plate attached to the first moved structure along the at least one guiding rail and a pneumatic first rotational actuator for rotating the first moved structure with respect to the first plate;
    a second module configured to provide both translational and rotational motions to a second moved structure, the second module including a pneumatic second structure translational actuator for translating a second plate attached to the second moved structure along the at least one guiding rail and a pneumatic second rotational actuator for rotating the second moved structure with respect to the second plate; and
    a third module configured to provide translational motion to a third moved structure, the third module including a pneumatic third translational actuator for translating a third plate attached to the third moved structure along the at least one guiding rail;
    wherein the structures comprising the first, second, and third modules are all made entirely from non-ferromagnetic materials.

3. The motive device of claim 2, wherein the first, second, and third moved structures are concentrically nested tubes, with a portion of the first moved structure located on a side of the first module longitudinally opposite the rear supporting plate being substantially located within lumens of the second and third moved structures and a portion of the second moved structure located on a side of the second module longitudinally opposite the rear supporting plate being substantially located within the lumen of the third moved structure.

4. The motive device of claim 2, wherein at least one of the first and second rotational actuators includes a linear actuator and a linear-to-rotary transmission.

5. The motive device of claim 2, wherein at least one of the first and second rotational actuators provides at least 360° (three hundred sixty degree) rotation of the respective first and second moved structures about a structure axis thereof.

6. The motive device of claim 2, wherein at least one pressure sensor and at least one pneumatic valve are pneumatically coupled to at least one module to provide pneumatic power thereto via pneumatic lines of suitable length, and wherein the at least one pressure sensor and pneumatic valve are housed in at least one of a Faraday cage and a separate room, wherein the Faraday cage and/or separate room is ferromagnetically shielded from the room housing an MRI machine with which the motive device is being used.

7. A system for operating an active cannula, the active cannula comprising innermost, middle, and outermost concentrically nested tubes, the system including the motive device of claim 2, wherein the first moved structure is the innermost tube, the second moved structure is the middle tube, and the third moved structure is the outermost tube.

8. The motive device of claim 1, wherein the at least one guiding rail includes a curvilinear profile to guide translational motion of the at least one module along a curvilinear path.

9. The motive device of claim 1, wherein the at least one module is entirely powered fluidically.

10. The motive device of claim 1, wherein the at least one module is powered by pneumatic pressure that is less than or equal to 50 (fifty) psi (pounds per square inch).

11. The motive device of claim 1, wherein the at least one guiding rail is substantially rigid and extends longitudinally through the module.

* * * * *

UNITED STATES PATENT AND TRADEMARK OFFICE
CERTIFICATE OF CORRECTION

PATENT NO. : 9,492,234 B2
APPLICATION NO. : 13/679512
DATED : November 15, 2016
INVENTOR(S) : David B. Comber et al.

Page 1 of 1

It is certified that error appears in the above-identified patent and that said Letters Patent is hereby corrected as shown below:

On the Title Page

Item (72) Inventors: please add: Robert J. Webster, Nashville, TN (US)

Signed and Sealed this
Twentieth Day of August, 2019

Andrei Iancu
*Director of the United States Patent and Trademark Office*